United States Patent [19]

Narang et al.

[11] Patent Number: 4,908,442
[45] Date of Patent: Mar. 13, 1990

[54] TETRA KETONE PORPHYRIN MONOMERS AND THE PROCESS OF PREPARATION THEREOF

[75] Inventors: Subhash C. Narang, Redwood City; Susanna Ventura, Sunnyvale, both of Calif.

[73] Assignee: General Petrochemical Industries, Limited, Tokyo, Japan

[21] Appl. No.: 247,590

[22] Filed: Sep. 23, 1988

[51] Int. Cl.⁴ .......................................... C07D 487/22
[52] U.S. Cl. ................................. 540/145; 204/157.71
[58] Field of Search ..................... 540/145; 204/157.71

[56] References Cited

U.S. PATENT DOCUMENTS 3,920,692 11/1975 Wiersdorff et al. ................. 540/145

OTHER PUBLICATIONS

M. J. Crossley et al., *Journal of Chemical Society, Chemical Communications*, 1987, pp. 39–40.
M. J. Crossley, Abstracts Booklet, 196th Annual American Chemical Society Meeting, Los Angeles, CA, Sep. 26–31, 1988, earlier published about July 15, 1988.

*Primary Examiner*—Richard L. Raymond
*Attorney, Agent, or Firm*—Phillips, Moore, Lempio & Finley

[57] ABSTRACT

The present invention relates to a tetraketone of the structure

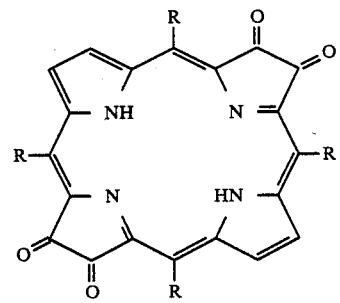

I or

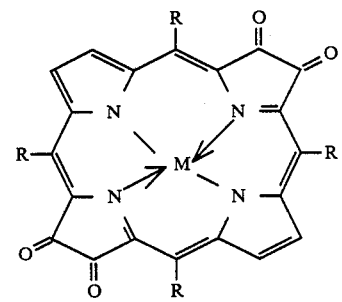

I(a)

wherein M is a metal atom and R is selected from phenyl, alkyl substituted phenyl or halogen substituted phenyl. The process to prepare this tetraketone is disclosed. The present invention also relates to a process to produce the tetraketone structure (I). The present invention also relates to the novel polymer of the structure

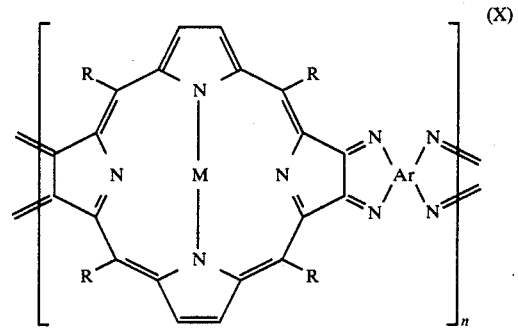

(X)

and to the process to produce this novel polymer. R is as defined hereinabove and Ar is a tetraamine substituted organic moiety having at least one aromatic ring. These polymers are useful as liquid crystals and in nonlinear optical devices.

14 Claims, 5 Drawing Sheets

FIG._1

FIG. 2
PREPARATION OF 5, 10, 15, 20-TETRAPHENYLPORPHYRIN
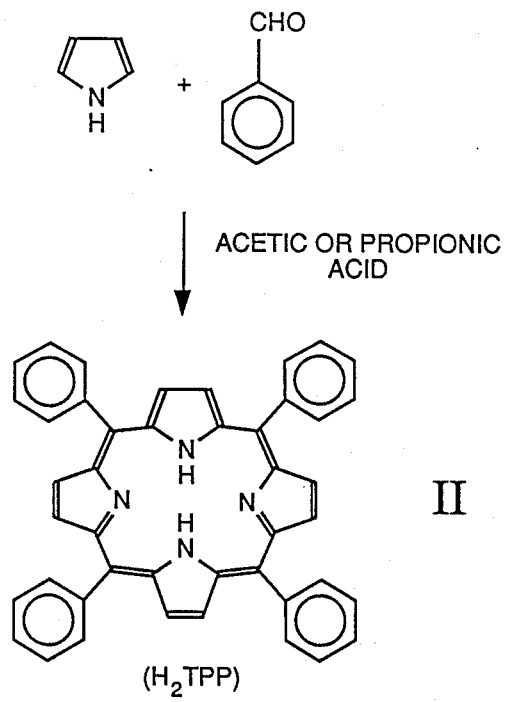
PURIFICATION FROM CHLORIN BY REACTION WITH DDQ
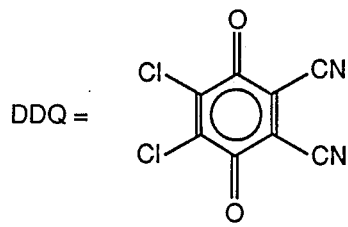

FIG._3
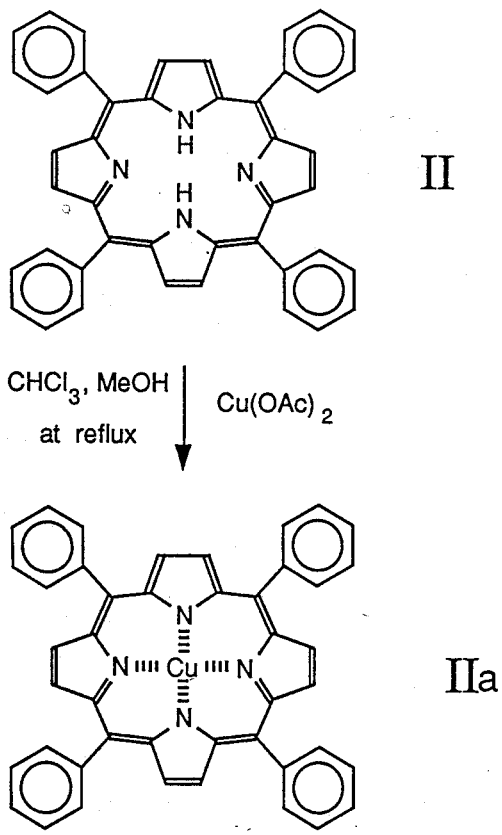

FIG._4
β-PYRROLIC NITRATION
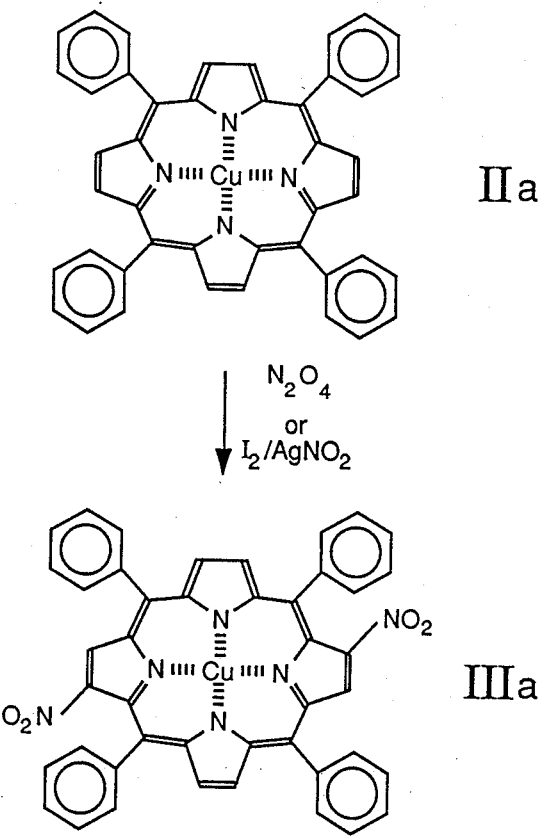

FIG._5
PREPARATION OF LADDER-LIKE METALLO-PORPHYRIN POLYMERS
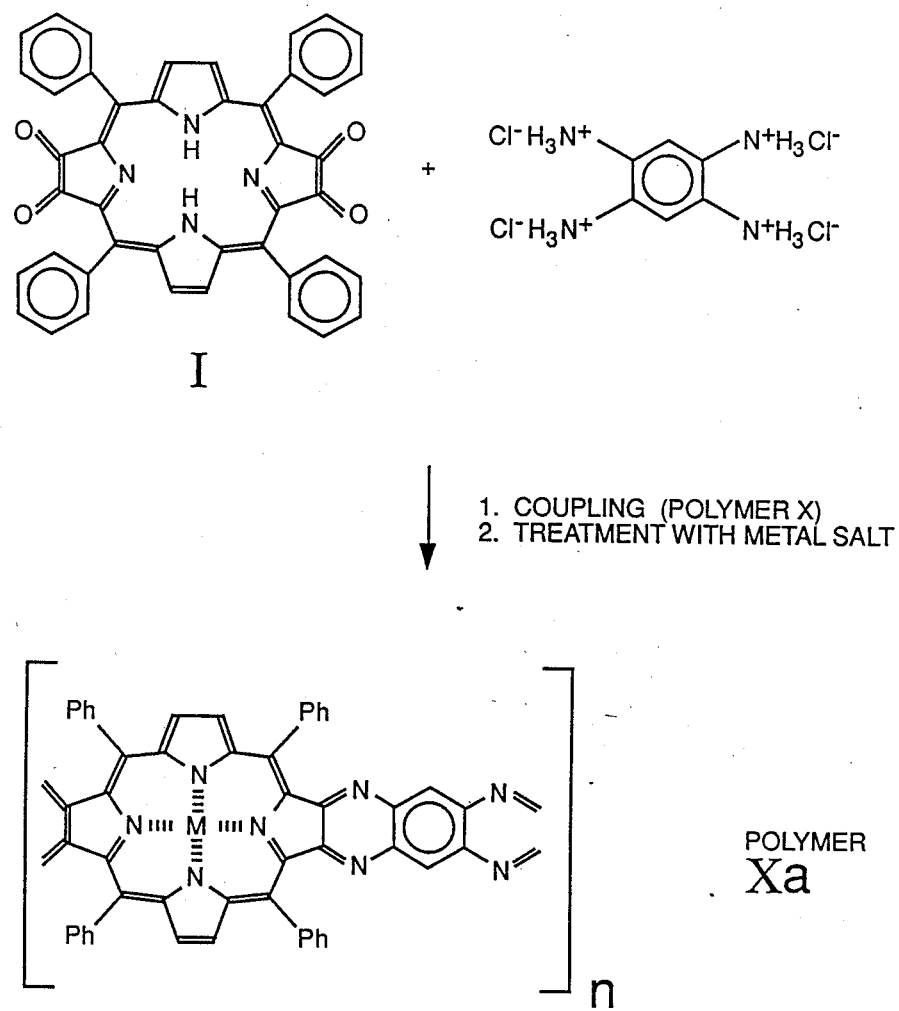

TETRA KETONE PORPHYRIN MONOMERS AND THE PROCESS OF PREPARATION THEREOF

BACKGROUND OF THE INVENTION

1. Field of Invention

The present invention relates to the synthesis of novel tetraketone porphyrin monomers and the linear porphyrin polymers produced when these porphyrins are condensed with tetramines. These polymers have a number of uses including non-linear optical materials, electrochromic polymers, semiconductor and electrically conducting polymers and advanced structural materials.

2. Description of Related Art

M. J. Crossley and Paul L. Burn published in the *Journal of Chemical Society, Chemical Communications*, 1987, p. 39–40, the synthesis of rigidly bridged bis-porphyrin systems involving the 2:1 condensation of an alpha dione (17,18-dioxochlorine) with a tetra-amine.

M. J. Crossley published about July 15, 1988 in the Abstracts Booklet of the 196th Annual Americal Chemical Society Meeting to be held in Los Angeles on September 26 to 31, 1988 (Abstract 60 (Inorganic Division)), showing only the structure of a linear ladder-type porphyrin polymer. No additional enabling experimental details were provided.

All reference articles or patents cited in this application are incorporated in their entirety herein by reference.

It is therefore desirable to produce a tetraketone porphyrin (metal) monomer and the polymers obtained by the reaction with tetraamines or tetraamine hydrohalides. The present invention accomplishes this objective.

SUMMARY OF THE INVENTION

The present invention relates to a tetraketoneporphyrin of the structure:

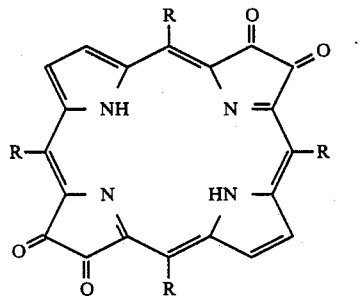
I or

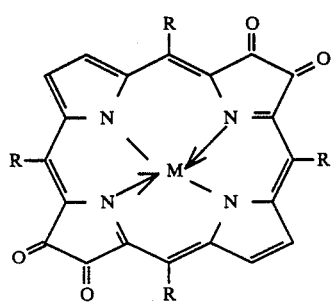
I(a)

wherein R is phenyl, alkyl substituted, or halogen phenyl, M is any metal atom, preferably selected from copper, iron, nickel, cobalt or manganese.

In another aspect, the present invention relates to a process for the preparation of a tetraketone of the structure:

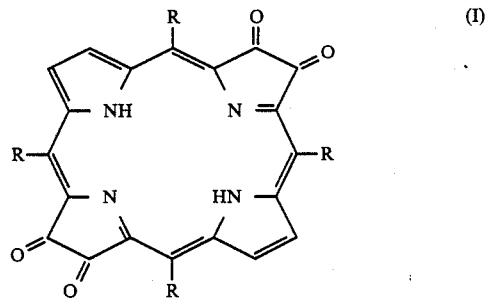
(I)

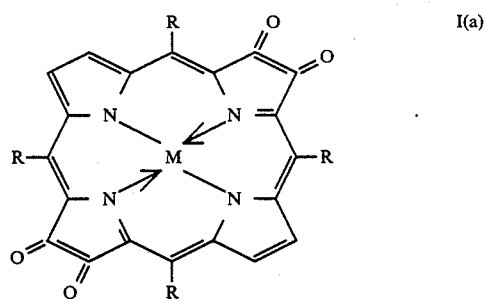
I(a)

wherein M and R are defined hereinabove, which process comprises:

(a) treating the chemical of the structure:

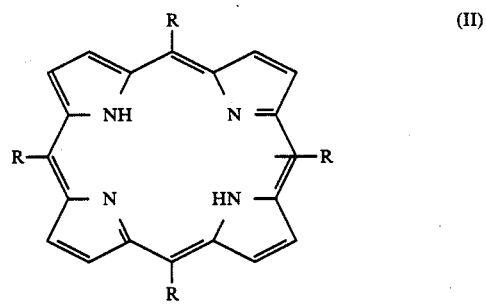
(II)

with an oxidizing agent to remove any dihydrochlorin impurity and produce compound II in at least 95% purity;

(b) contacting the compound II of step (a) with a metal salt to produce the metal porphyrin II(a):

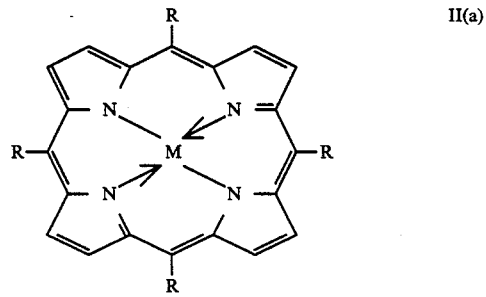
II(a)

(c) contacting the compound II(a) with $N_2O_4$ to produce the dinitro-III(a) of the structure;

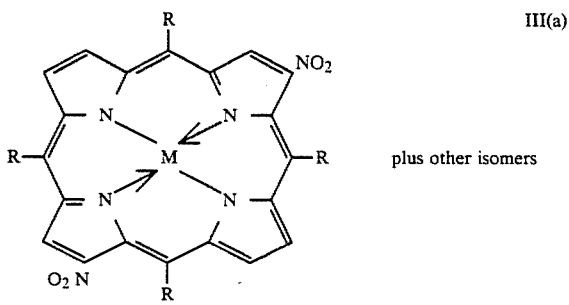

plus other isomers (d) contacting the dinitro compound III(a) of step (c) with concentrated sulfuric acid to produce the dinitro demetallized compound III:

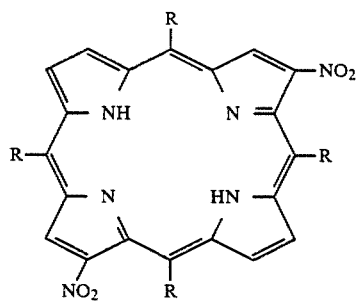

(e) reducing the dinitro-III of step (d) with a reducing agent to produce the diamino-IV of the structure:

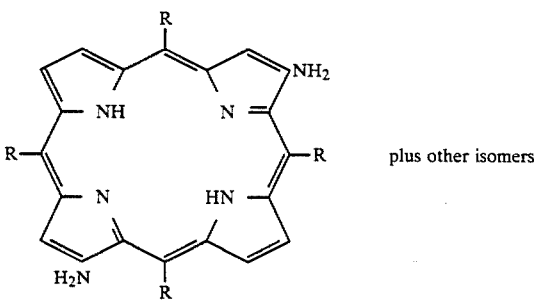

plus other isomers (f) contacting the diamino-IV of step (e) with an oxidizing agent to produce the tetraketone of structure I.

In another aspect, the present invention relates to the aforementioned process, which further includes:

(g) contacting the compound of step (f) with a metal salt to produce a metal porphyrin of the structure:

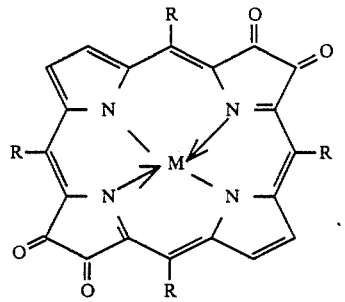

where M and R are as defined hereinabove.

In another aspect, the present invention relates to an electrically conductive polymer of the structure Xa:

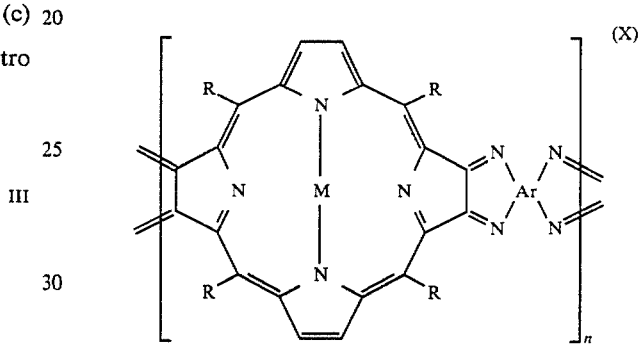

wherein

M is a metal atom, preferably selected from copper, iron, cobalt, nickel, or manganese;

R is selected from phenyl, alkyl substituted phenyl, halogen substituted phenyl; and Ar is selected from the group consisting of:

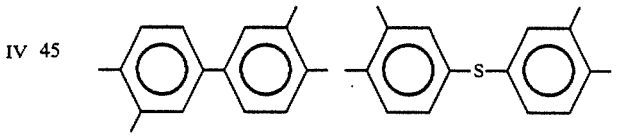

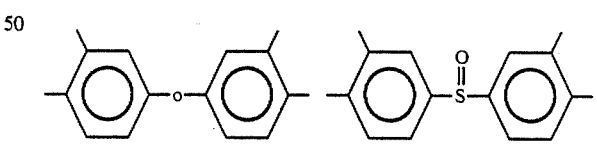

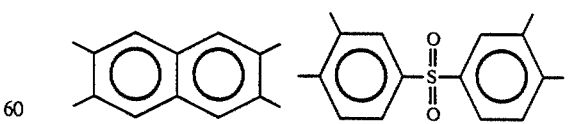

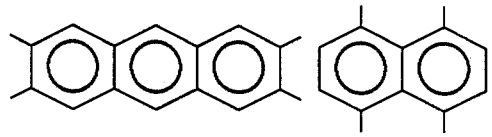

-continued

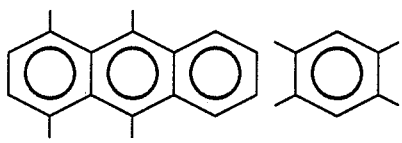

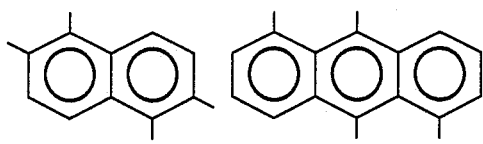

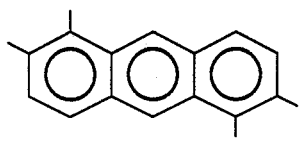

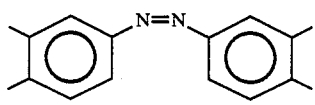

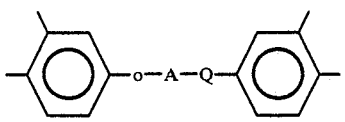

when Q is oxygen, A is (CH$_m$—, —(CH$_2$CH(CH$_3$))$_m$—,

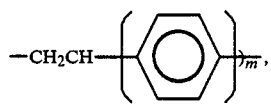

—(CF$_2$CF$_2$)$_m$—, or —(CF$_2$CF(CF$_3$))$_m$—; or when Q is a direct carbon-carbon bond, A is —(CH$_2$CH$_2$O)$_m$—, —(CH$_2$CH(CH$_3$)O)$_m$—, or —(SiR'$_2$O)$_m$— wherein R' is methyl, ethyl, propyl or butyl and m is 10 to 10,000.

In another aspect, the present invention relates to a process to produce a linear polymer of the structure:

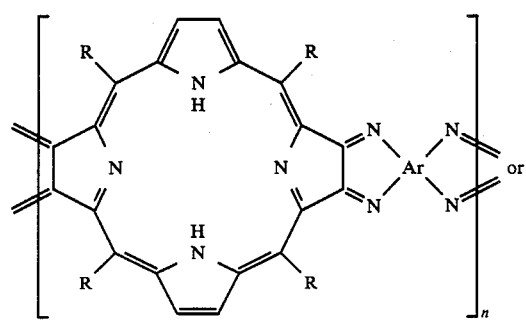

-continued

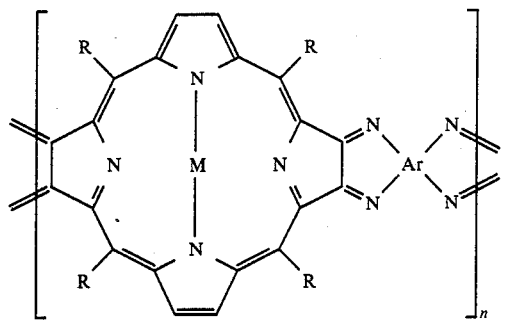

wherein

M is selected from any metal atom, preferably copper, iron, cobalt, nickel, or manganese;

Ar is as defined hereinabove;

R is selected from phenyl, alkyl substituted phenyl and halogen substituted phenyl, which process comprises:

(a) contacting a tetraketone of structure I:

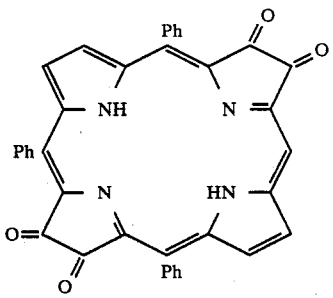

with a tetraamine or a tetraamine hydrohalide selected from the group of structures consisting of:

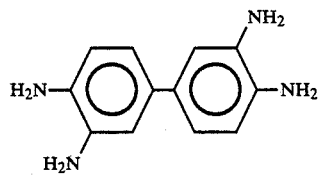

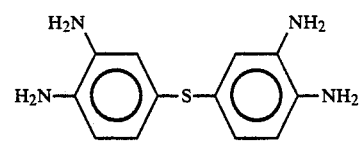

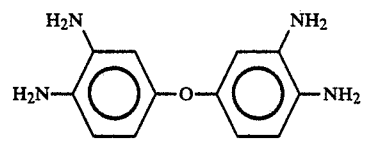

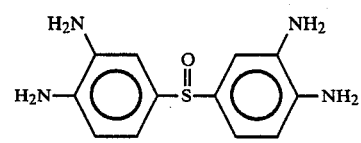

-continued

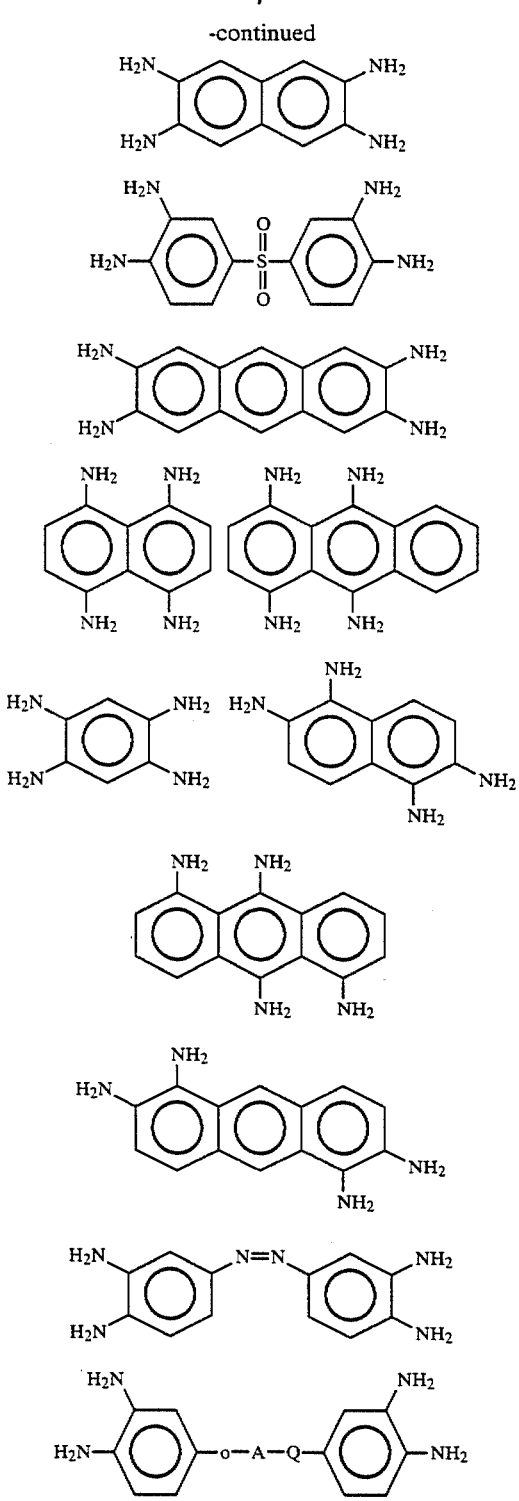

wherein when Q is oxygen (O), A is (—CH$_2$)$_m$—, —(CH$_2$CH(CH$_3$))$_m$—,

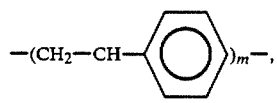

—(CF$_2$CF$_2$)$_m$—, or —(CF$_2$—CF(CF$_3$))$_m$—; or when Q is a direct carbon-carbon bond, A is (CH$_2$CH$_2$O$_m$—, —(CH$_2$CH(CH$_3$)O$_m$—, or —(SiR'$_2$O)m—, wherein R' is methyl, ethyl, propyl, or butyl and m is 10 to 10,000.

(b) maintaining the solution of step (a) for between about 0.1 to 6 days at ambient temperature or higher and recovering the polymer of structure X.

BRIEF DESCRIPTION OF THE FIGURES

FIG. 2 shows a reaction for the synthesis and purification the starting material 5, 10, 15, 20 tetra-phenylporphyrin (II).

FIG. 3 shows a reaction for the synthesis of a copper (II) porphyrin intermediate (IIa).

FIG. 4 shows a reaction for the synthesis of a dinitroporphyrin intermediate (IIIa).

FIG. 5 shows a general reaction for the production of a linear ladder-like metalloporphyrin polymer Xa.

DETAILED DESCRIPTION OF THE INVENTION AND PREFERRED EMBODIMENTS

Definitions

Figure 1:
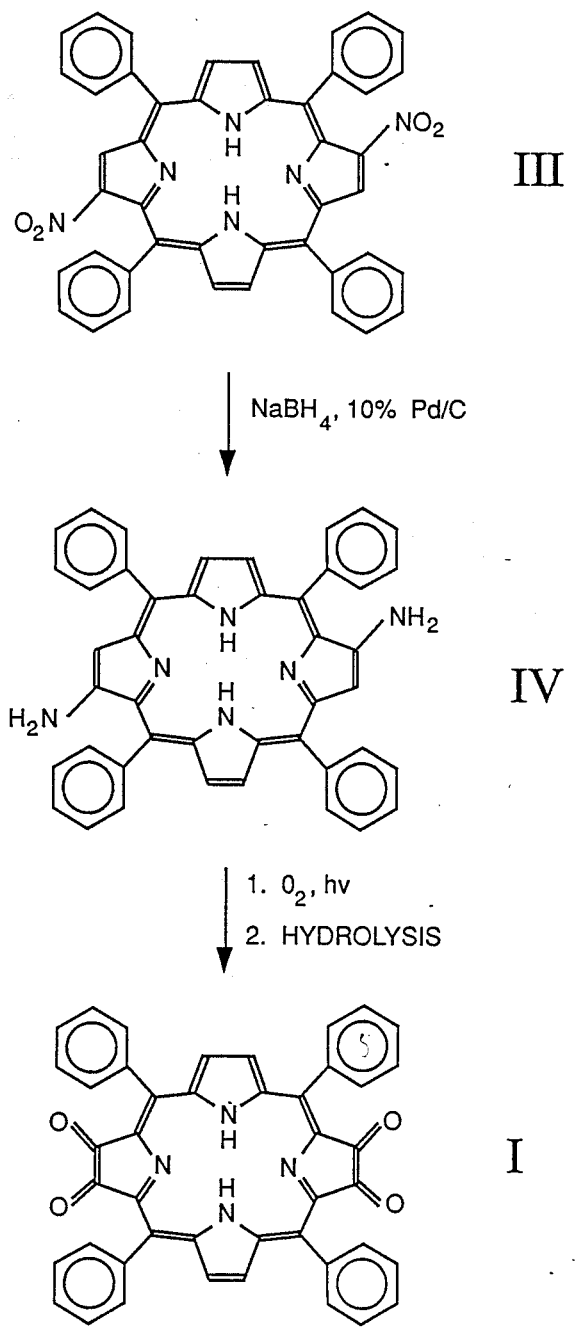
FIG. 1 shows a reaction sequence for the synthesis of a novel tetra-ketoporphyrin (I), where R is phenyl.

As used herein:

"Metal(s)" refers to any atom of the Periodic Table having the properties of a metal. These include preferably all transition metals, actinides and lanthanides. More preferably copper, iron, cobalt, nickel or manganese are used. See *Porphyrins and Metalloporphyrins* by K. M. Smith Elsevier/North-Holland Biochemical Press 1976, which is incorporated herein by reference.

"Metal salt" refers to an organic or inorganic salt used to treat a dihydro-porphyrin structure to produce the corresponding metal porphyrin compound. Acetates and propionates are preferred.

Synthesis of the Tetraketoporphyrin Monomer.

Referring to FIGS. 1 to 5, is described the synthetic route to obtain a tetraketoporphyrin monomer, Compound I, e.g., where R is phenyl.

Tetraphenylporphyrin (Compound II): The preparation of Compound II is obtained according to the prodecure reported by A. D. Adler, F. R. Longo, J. D. Finarelli, J. Goldmacher, J. Assour, and L. Korsakoff, *Journal of Organic Chemistry*, 32, 476 (1967), which is incorporated herein by reference. Equimilar quantities of pyrrole and a benzaldehyde are combined using acetic acid or propionic acid.

Different porphyrin compounds are prepared by replacing the benzaldehyde with stoichiometrically equivalent amounts of 4-methylbenzaldehyde, 3,5 dimethylbenzaldehyde, 4-chlorobenzaldehyde, 4-methoxybenzaldehyde, and the like.

Metal Tetraphenyl Porphyrin (IIa): Compound II is combined with a metal acetate, in a solvent of, for example, chloroform and methanol. The solution is heated at reflux for between about 15 and 30 min. After cooling, the solid product IIa is obtained by filtration. Different metal acetate reagents will produce different metal porphyrins. Preferred metals include for example, copper, iron, nickel, cobalt, or manganese. Copper is more preferred.

Metal(II) Dinitrotetraphenylporphyrins and their Demetallation: Compound IIIa: The metal II porphyrin, Compound IIa, is dissolved in excess dipolar aprotic solvent, such as methylene chloride, chloroform or the like, in an inert atmosphere, such as nitrogen or argon. Solvent and a nitrating agent, such as dinitrogen tetraoxide are combined. The nitrating agent solution is slowly added to the methylene chloride solution of the porphyrin. Next, the crude product is contacted with excess concentrated sulfuric acid. The produce is carefully poured onto ice/water and extracted. The solid product is Compound II. The infrared, mass and proton nuclear magnetic spectral data are consistent with the dinitroderivative attributes.

Diaminotetraphenylporphyrin—Compound IV: The dinitroporphyrins (Compound III) is dissolved in an aprotic solvent in an inert atmosphere. An alcohol, such as methanol, is added. A catalyst, such as palladium on carbon is added to the Compound III solution followed by a borohydride reducing agent, such as sodium borohydride. After filtration and removal of the solvent, the crude residue is purified by column chromatography using a polar solvent to produce diamino compound IV.

Tetraketotetraphenylporphyrin—Compound I: Compound IV is dissolved in an aprotic solvent. Oxygen gas is bubbled into the solution which is simultaneously irradiated with tungsten sun lamp. The solution obtained is purified by chromatography on silica gel using methylene chloride/hexane or benzene/ethyl ether as solvent.

The novel monomer—the tetraketone I where R is phenyl is obtained. NMR and IR spectral analysis are consistent with the tetraketone structure (I) wherein the two alpha diones moieties are not on adjacent porphyrin groups. This result is unexpected.

At the nitration step above, a number of isomers are formed. However, it is found that it is not necessary to separate these isomers. After, the oxidation to form the desired tetraketone I, the isomeric impurities are easily separated by chromatography.

Preparation of Cu(II) Tetraketone (Ia)—Tetraketone I is dissolved in an aprotic solvent and is heated to reflux. Metal acetate (e.g. copper) in alcohol is added and the solution is refluxed under inert gas. The reaction is complete in 3 to 30 hr. After normal workup, the metal containing compound I(a) is obtained.

Synthesis of Metal (II) Polymer X—The metal ketone I(a) is dissolved in dipolar aprotic solvent dimethylformamide, and pyridine. The tetraamine —Ar hydrochloride is added. After, 2 days at ambient temperature in the dark, the reaction is complete. The metal containing polymer X(a) is obtained having a mean molecular weight of greater than 10,000 daltons.

Synthesis of Polymer X(a)—The polymer synthesized by condensation of the tetaketone I and tetraamino aromatic compound (Ar) are dissolved in dipolar aprotic solvent and heated to 90°-100° C. under inert gas. Metal (copper) acetate is added. After 20 hr. at reflux (90°-100° C.), the reaction mixture is cooled. UV-VIS confirmmed that the polymer metal (II) complex porphyrin had formed.

The compounds of the structure:

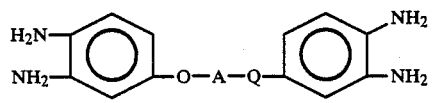

VI are prepared by first treating at least two moles of paradinitrobenzene with one mole of a diol or diol sodium salt in the presence of a base such as potassium tertiary butoxide at about 80° C. for 1 to 4 hours to produce diether VI.

Alternatively, diether VI is prepared by reacting 2 moles of para nitrophenol with a dihalogen substituted X-A-X where X is Cl, Br or I in the presence of base such as potassium tertiary butoxide.

The coupled product VI is next contacted with excess stannus chloride in about 1 to 2N hydrochloric acid at ambient temperature overnight to produce compound VII.

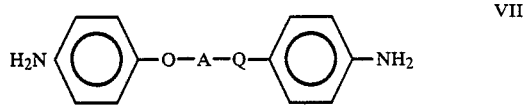

VII

Compound VII is contacted with a mixture of 70% nitric acid and 96% sulfuric acid at about −20° to 0° C. for 1-4 hrs. After normal workup, Compound VIII is obtained:

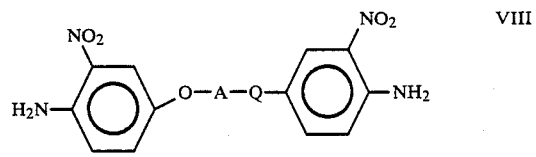

VIII

Compound VIII is contacted again with stannous chloride in 1 to 2N hydrochloric acid at ambient temperature to produce compounds of the tetraamine structure desired.

Formation of Linear Porphyrin Polymers—Compound I is contacted with a tetraamine or amine hydrohalide in the presence of a base and a dipolar aprotic sovlent in the absence of light in an inert atmosphere. The polymer obtained is subjected to gel permeation chromatography to determine the mean molecular weight of the polymer. Usually a polymer having a molecular weight of about 20,000 daltons or greater is obtained.

These polymers are useful as liquid crystal polymers. Initially, the polymers are evaluated by thermal gravimetric analysis (TGA) and differential scanning calorimetry (DSC). The rheological behavior is studied using a rheometrics mechanical spectrometer.

The electrical conductivity of the polymers is determined by the four-point probe method using cast films.

Changes in UV-visible spectra of the polymers with applied potential are determined by casting polymer films on indium-tin oxide (ITO), platinum or gold-coated semitransparent electrodes. Reversibility and response time are determined as is described in published methods.

The materials, chemicals or reagents for the present invention are commercially available from chemical supply houses such as Aldrich Chemical Company of Milwaukee, Wis. Other suppliers can be located in Chem Sources, U.S.A., which is published annually by Directories Publishing, Inc. of Columbia, S.C. The chemicals are usually used without further purification unless otherwise noted.

The following Examples are presented to be illustrative and explanatory only. They are not to be construed as limiting in any way.

EXAMPLE I

Tetraphenylporphyrin (II)

(a) The preparation of (II) is accomplished according to the procedure described by A. D. Adler, F. R. Long, J. D. Finarelli, J. Goldmacher, J. Assour, L. Korsakoff, *Journal of Organic Chemistry*, 32, (1967) 476, which is incorporated herein by reference. This procedure uses pyrolle and benzaldehyde in acetic or propionic acid solution. (FIG. 3).

(b) The reaction of Example 1(a) is repeated except that benzaldehyde is replaced with a stoichiometrically equivalent amount of 4-methylbenzaldehyde. The corresponding tetra(4-methylphenyl)porphyrin is obtained.

EXAMPLE 2

Copper (II) Tetraphenylporphyrin (IIa)

(a) Tetraphenylporphyrin (II) (16.80 g., 27.3 mmol) is dissolved in 2000 ml of chloroform under reflux. Copper (II) acetate monohydrate (5.45 g., 27.3 mmol) is dissolved in 600 ml of methanol, and added dropwise to the methylene chloride solution in about 15 minutes. After the addition is over, the solution is refluxed for 30 minutes and cooled. The completion of the reaction is checked by UV-VIS spectrophotometry. The product IIa is isolated by evaporation of the solvents.

(b) The reaction of Example 2(a) is repeated except that the copper (II) acetate is replaced with a stoichiometrically equivalent amount of iron (II) nitrate. The corresponding iron (II) porphyrin is produced.

EXAMPLE 3

Copper (II) Dinitrotetraphenylporphyrins (IIIa)

(a) Copper (II) tetraphenylporphyrin (IIa) (2.0 g., 2.96 mmol) is dissolved in 300 ml of anhydrous methylene chloride under a nitrogen blanket. The solution is a dark red color.

In a glass cylinder 3.27 g. of dinitrogen tetraoxide ($N_2O_4$) are transferred, and anhydrous methylene chloride is added until the total volume is 20 ml. 3.4 Ml of the methylene chloride solution are transferred by a double tip needle to an addition funnel and dropped into the methylene chloride solution of compound IIa. In a few minutes after the addition of $N_2O_4$ is complete, the reaction solution turns green. The reaction progress is checked by thin layer chromatography after 30 min. A principle product III(a) is present. The UV-VIS spectrum of the crude reaction shows strong absorbance at 432 nanometers (nm).

EXAMPLE 4

Dinitrotetraphenylporphyrins (IIIa)

(a) The crude Compound IIIa (22.23 g) is dissolved in methylene chloride (800 ml). To this solution is added 100 ml of sulfuric acid (96%), and the mixture is stirred for 15-20 minutes. Next, the reaction mixture is poured into ice-water, the aqueous layer is extracted several times with methylene chloride. The organic layer and washes are washed with water and 5% sodium bicarbonate, and dried over magnesium sulfate. FT IR shows absorption at 1510 cm$^{-1}$ and 1340 cm$^{-1}$. (—$NO_2$ asymmetrical and symmetrical stretching). Mass spectrometry (field ionization) showed essentially Compound III; m/e=704. Other isomers are present.

EXAMPLE 5

DIAMINOTETRAPHENYLPORPHYRIN IV

Compound III 800 mg (1.14 mmol) is dissolved in 200 ml of methylene chloride under argon. Methanol (50 ml) is added, and the solution remains homogeneous. Palladium (10%) on carbon (1.96 g.) added, followed by solid sodium borohydride (2.08 g., 54 mmol) is added in small portions over about 15 min. The solution, which first turns to red then to red-brown, is stirred for about 40 min. Anhydrous methylene chloride (200 ml) is added and the solution is filtered through Celite. The filtrate is removed under reduced pressure. The residue is stirred with 200 ml of anhydrous methylene chloride and filtered again. The filtrate is concentrated again using reduced pressure, and the crude residue, about 1 g., is recovered. The diaminoporphyrins are purified by flash chromatography on silica gel using methylene chloride as eluent. The infrared, the proton magnetic resonance and mass spectra are consistent with the diamino structure IV.

EXAMPLE 6

TETRAKETOTETRAPHENYLPORPHYRIN (I)

(a) To a 300 ml flask are added the diaminotetraphenylporphyrin isomers IV (200 mg) and 80 ml of methylene chloride (anhydrous). Oxygen is bubbled into the solution which is irradiated with a solar lamp. The reaction progress is monitored by TLC (silica gel), eluent: methylene chloride or methylene chloride/hexane (7/3:v/v). From the TLC, after 4 hr., the diamino compounds IV appear to have been completely converted. The methylene chloride solution is stirred overnight with 1 g. silica gel in the air. The tetraketotetraphenylporphyrin (I) is isolated from the oxide product by preparative, centrifigally accelerated, thin layer chromatography, using a rotor coated by a silica gel layer 4 mm. thick and benzene/1% ethyl ether as eluent. The spectroscopic analysis (VIS, IR, $^1$H—NMR) are consistent with the attribution of the structure (I).

EXAMPLE 7

POLYMERIZATION OF TETRAKETOTETRAPHENYLPORPHYRIN I AND A TETRAMINETETRAHYDROCHLORIDE (a) Compound I (8.5 mg., 0.0130 mmal) and 1,2,4,5-tetraaminobenzene tetrahydrochloride (3.73 mg., 0.0131 mmol), dimethylformamide (1 ml) and pyridine (0.5 ml) are combined producing a homogeneous solution which is kept under an argon blanket in the dark at ambient temperature. After 112 hr., the solvent is distilled off under vacuum and the linear ladder polymer is isolated. The polymer is characterized by gel permeation chromatography (gpc). The portion of polymer soluble in dimethyformamide has a molecular weight of about 20,000 daltons, or greater computed against monodispersed polystyrene calibration standards. The remaining portion is insoluble in the characterization solvent and therefore has higher molecular weight.

(b) The polymerization reaction of Example 7(a) os repeated except that the tetraaminobenzenetetrahydrochloride is replaced by:

3,4,3',4'-tetraaminobiphenyl;
3,4,3',4'-tetraaminobiphenyloxide;
3,4,3',4'-tetraaminobiphenylsulfide;
3,4,3',4'-tetraaminobiphenylsulfone;

3,4,3',4'-tetraaminobiphenylsulfoxide;
3,4,3',4'-tetraaminobiphenylazine;
2,3,6,7-tetraaminonaphthalene;
1,2,5,6-tetraaminonaphthalene;
1,4,5,8-tetraaminonaphthalene;
2,3,7,8-tetraaminoanthracene;
1,2,6,7-tetraaminoanthracene;
1,4,5,10-tetraaminoanthracene;
1,5,6,10-tetraaminoanthracene;
2,3,7,8-tetraaminoanthracene; or

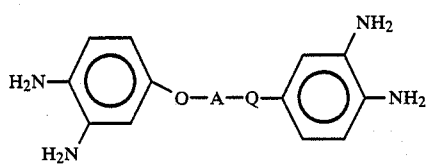

wherein when Q is oxygen (O), A is selected from —(CH$_2$)$_m$—; —(CF$_2$)$_m$—; —(CF$_2$CF(CF$_3$))$_m$—,

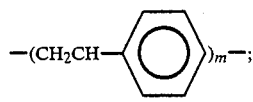

or when Q is a direct carbon-carbon bond, A is selected from —(CH$_2$CH$_2$O)$_m$—, —(CH$_2$CH(CH$_3$))$_m$—, —(CF$_2$CF(CF$_3$)O)$_m$—, or —(Si(R'$_2$)O$_m$—, wherein R' is methyl, ethyl, propyl, butyl or phenyl, and m is between about 1 and 10,000, wherein each of the above tetraamines are present as the tetrahydrogen chloride.

EXAMPLE 8

Preparation of Cu(II) Tetraketone

The tetraketone (30 mg., 4.45. mmol) is dissolved in chloroform (5.0 ml) and the solution is refluxed. To the solution is added copper acetate in methanol dropwise (10 mg. in 2.0 ml of methanol). The reaction mixture is refluxed under nitrogen. The copper complexation is followed by UV-VIS spectroscopy, by monitoring the shift of the lambda max from 384 nm. to 418 nm. After 20 hours the conversion is complete. The solvents are evaporated under vacuum, the residue is dissolved in methylene chloride and washed with water. The organic layer is dried over MgSO$_4$, and the product, I(a), is recovered by evaporation of the solvent.

EXAMPLE 9

Synthesis of the Cu(II) Polymer

The Cu(II) tetraketone (20 mg., 0.027 mmol) is dissolved in 2 ml of dimethylformamide and 1 ml of pyridine. To this solution 1,2,4,5-benzenetetramine tetrahydrochloride (7.72 mg., 0.027 mmol) is added. The solution is stirred in the dark, under nitrogen for 2 days. By gel permeation chromatography (gpc) a polymer with molecular weight 15,000 daltons is detected.

EXAMPLE 10

Preparation of Cu(II) Polymer

The polymer is synthesized by condensation of the tetraketone with 1,2,4,5-benzenetetramine tetrahydrochloride (5 mg.) is dissolved in 2.0 ml. of dimethyformamide and heated up to 90°–100° C. under nitrogen. To this solution copper acetate is added (10 mg. in 1.0 ml of dimethylformamide). The reaction solution is held at 90°–100° C. for 20 hours. The formation of the Cu(II) complex of the polymer is verified by a change in the UV-VIS spectrum of the compound in dimethylformamide.

In the polymerization of the monomers to obtain Polymer X (no metal present) or Polymer Xa (metal present), n is the degree of polymerization. "n" is between about 2 and 1000, preferably between about 4 and 500, and most preferably between about 5 and 100. "n" is especially preferred between 5 and 20.

While only a few embodiments of the invention have been shown and described herein, it will become apparent to those skilled in the art that various modifications or changes can be made in the process to produce tetraketoporphyrins and the porphyrin-based metal polymers thereof without departing from the spirit and scope of the present invention. All such modifications and changes coming within the scope of the appended claims are intended to be carried out thereby.

We claim:

1. A tetraketone of structure:

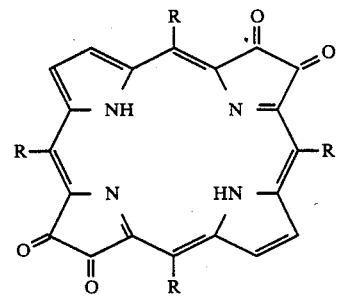

or

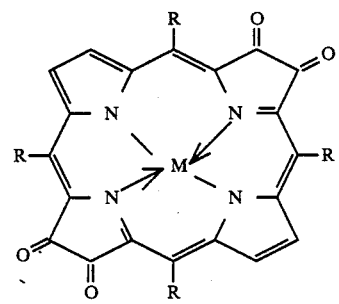

wherein M is a metal atom, and

R is phenyl, alkyl substituted phenyl or halogen substituted phenyl.

2. The tetraketone I(a) of claim 1 wherein M is selected from copper, iron, nickel, cobalt or manganese.

3. The tetraketone of claim 2 wherein M is copper.

4. The tetraketone (I) of claim 1.

5. The tetraketone of claim 4 wherein R is phenyl.

6. A process for the preparation of a tetraketone of the structure:

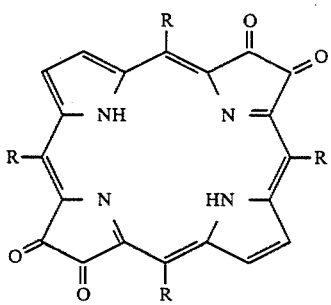

wherein R is selected from phenyl, alkyl substituted phenyl, or halogen substituted phenyl, which process comprises:

(a) treating the chemical of the structure:

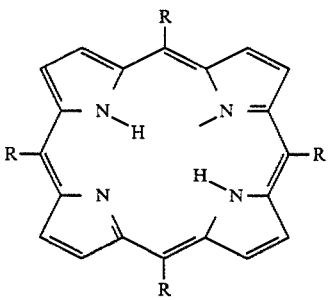

with an oxidizing agent to remove any dihydrochlorin impurity and produce chemical II in at least 95% purity:

(b) conducting the compound of step (a) with a metal salt to produce a porphyrin incorporating M;

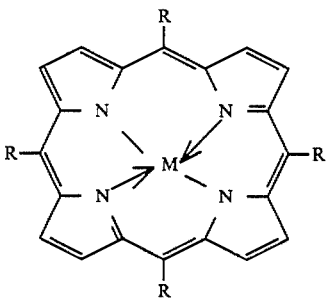

(c) contacting the purified chemical II(a) with $N_2O_4$ to produce the dinitro-III(a) of the structure:

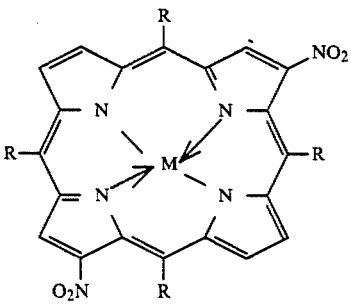

plus other isomers (d) contacting the dinitro compound of step (c) with concentrated sulfuric acid to produce the dinitro demetallated compound III:

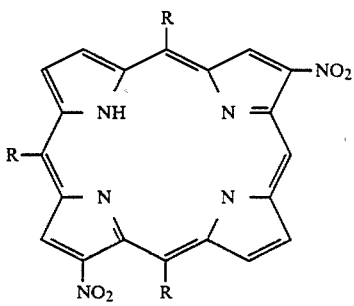

plus other isomers (e) reducing the dinitro-III of step (d) with a reducing agent to produce the diamino-IV of the structure:

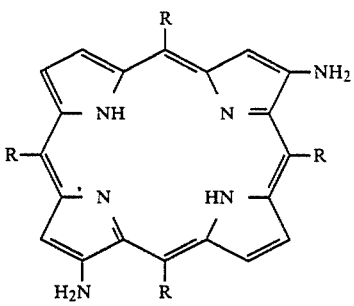

plus other isomers; and (f) contacting the diamino-compound of step (e) with an oxidizing agent to produce the tetraketone of structure I.

7. The process of claim 6 wherein R is phenyl.
8. The process of claim 6 wherein M is copper cobalt.
9. The process of claim 6 which further includes:
step (g) wherein the porphyrin of step (f) is contacted with a metal salt to produce the metal porphyrin compound of structure:

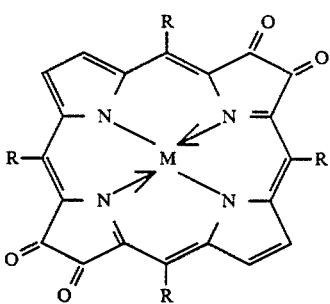

10. The process of claim 6 wherein
in step (a) the oxidizing agent is dichlorodicyanoquinone,
in step (b) the metal salt is selected from the group consisting of copper, iron, nickel, cobalt or manganese,
in step (e) the reducing agent is palladium on carbon followed by sodium borohydride, and in step (f) the oxidizing agent is a combination of light energy and oxygen.

11. A process for the preparation of a tetraketone of the structure:

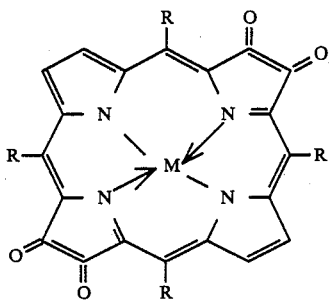

I(a)

wherein R is selected from phenyl, alkyl substituted phenyl, or halogen substituted phenyl, wherein M is a metal atom, which process comprises:

(a) treating the chemical of the structure:

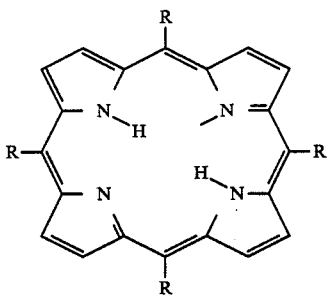

II with an oxidizing agent to remove any dihydrochlorin impurity and produce chemical II in at least 95% purity:

(b) contacting the compound of step (a) with a metal salt to produce a porphyrin incorporating M;

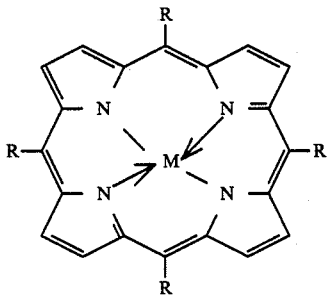

IIa (c) contacting the purified chemical II(a) with $N_2O_4$ to produce the dinitro-III(a) of the structure:

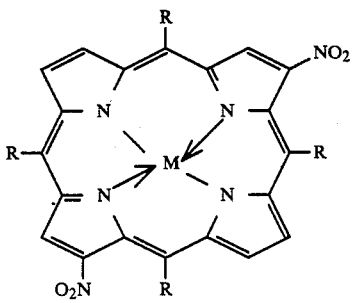

III(a)

plus other isomers (d) contacting the dinitro compound of step (c) with concentrated sulfuric acid to produce the dinitro demetallated compound III:

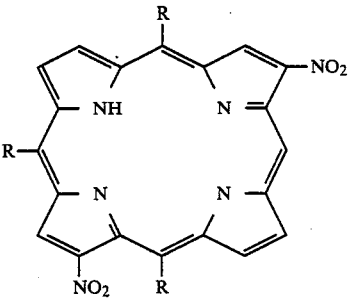

III plus other isomers (e) reducing the dinitro-III of step (d) with a reducing agent to produce the diamino-IV of the structure:

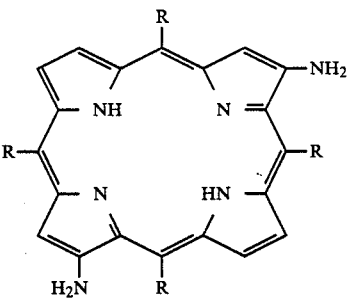

IV plus other isomers;

(f) contacting the diamino-compound of step (e) with an oxidizing agent to produce the tetraketone of structure

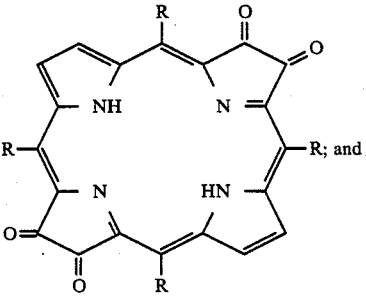

I (g) contacting the porphyrin of step (f) with a metal salt to produce the metal porphyrin compound of structure Ia.

12. The process of claim 11 wherein R is phenyl.
13. The process of claim 11 wherein M is copper or cobalt.
14. The process of claim 11 wherein
in step (a) the oxidizing agent is dichlorodicyanoquinone,
in step (b) the metal salt is selected from the group consisting of copper, iron, nickel, cobalt or manganese,
in step (e) the reducing agent is palladium on carbon followed by sodium borohydride, and
in step (f) the oxidizing agent is a combination of light energy and oxygen.

* * * * *